(12) United States Patent
Rofe et al.

(10) Patent No.: US 12,295,722 B2
(45) Date of Patent: May 13, 2025

(54) PRESSURE SENSING MAT

(71) Applicant: Wellsense, Inc., Birmingham, MI (US)

(72) Inventors: Arik Rofe, Ma'ale HaHamisha (IL); Asaf Brosh, Rosh Tzurim (IL); Oola Greenwald, Mevasseret Zion (IL)

(73) Assignee: Wellsense, Inc., Birmingham, MI (US)

( * ) Notice: Subject to any disclaimer, the term of this patent is extended or adjusted under 35 U.S.C. 154(b) by 643 days.

(21) Appl. No.: 17/432,282

(22) PCT Filed: Feb. 24, 2020

(86) PCT No.: PCT/US2020/019486
§ 371 (c)(1),
(2) Date: Aug. 19, 2021

(87) PCT Pub. No.: WO2020/172662
PCT Pub. Date: Aug. 27, 2020

(65) Prior Publication Data
US 2022/0125335 A1   Apr. 28, 2022

Related U.S. Application Data

(60) Provisional application No. 62/809,158, filed on Feb. 22, 2019.

(51) Int. Cl.
*A61B 5/103* (2006.01)
*A61B 5/00* (2006.01)
(Continued)

(52) U.S. Cl.
CPC ............ *A61B 5/1036* (2013.01); *A61B 5/447* (2013.01); *A61B 5/6892* (2013.01); *B32B 5/26* (2013.01);
(Continued)

(58) Field of Classification Search
None
See application file for complete search history.

(56) References Cited

U.S. PATENT DOCUMENTS

2009/0216466 A1   4/2009   Altman et al.
2011/0271772 A1   11/2011  Parks et al.
(Continued)

FOREIGN PATENT DOCUMENTS

CA   2541468 A1   9/2006
CN   101421692 A   4/2009
(Continued)

OTHER PUBLICATIONS

First Search in Chinese Application No. 202080016078, issued Sep. 29, 2022, 3 pages.

*Primary Examiner* — Alexander S Thomas
(74) *Attorney, Agent, or Firm* — Brooks Kushman P.C.

(57) ABSTRACT

The pressure sensing mat including a first portion and a second portion. The first portion may include a first conductive layer that may be sandwiched between a first non-conductive layer and a non-conductive layer that define a first set of channels that may at least partially enclose a first conductive strip that may extend in a first direction. The second portion may include a second conductive layer that may be sandwiched between a third non-conductive layer and a fourth non-conductive layer that may define a second set of channels that may at least partially enclose a second conductive strip that may extend in a second direction. The first conductive strip and the second conductive strip may form a capacitor that may be configured to provide a capacitance indicative of a pressure applied to the capacitor.

27 Claims, 10 Drawing Sheets

(51) Int. Cl.
 *B32B 5/26* (2006.01)
 *G01L 1/14* (2006.01)
 *G01L 5/00* (2006.01)

(52) U.S. Cl.
 CPC ............ *G01L 1/146* (2013.01); *G01L 5/0014* (2013.01); *A61B 2562/0247* (2013.01); *A61B 2562/046* (2013.01)

(56) References Cited

U.S. PATENT DOCUMENTS

| | | | |
|---|---|---|---|
| 2013/0317393 A1* | 11/2013 | Weiss | A61B 5/447 |
| | | | 600/587 |
| 2015/0320352 A1 | 11/2015 | Ben Shalom et al. | |
| 2017/0010746 A1 | 1/2017 | Hotelling et al. | |
| 2018/0160911 A1 | 6/2018 | Fu et al. | |
| 2019/0049322 A1 | 2/2019 | James et al. | |

FOREIGN PATENT DOCUMENTS

| | | | |
|---|---|---|---|
| CN | 105553323 A | 5/2016 | |
| CN | 109000829 A | 12/2018 | |
| DE | 202010008269 U1 | 10/2010 | |
| GB | 1438690 A | 6/1976 | |
| JP | 2005303314 A | 10/2005 | |
| JP | 2012523299 A | 10/2012 | |
| JP | 2018112489 A | 7/2018 | |
| WO | 2019019956 A1 | 1/2019 | |

\* cited by examiner

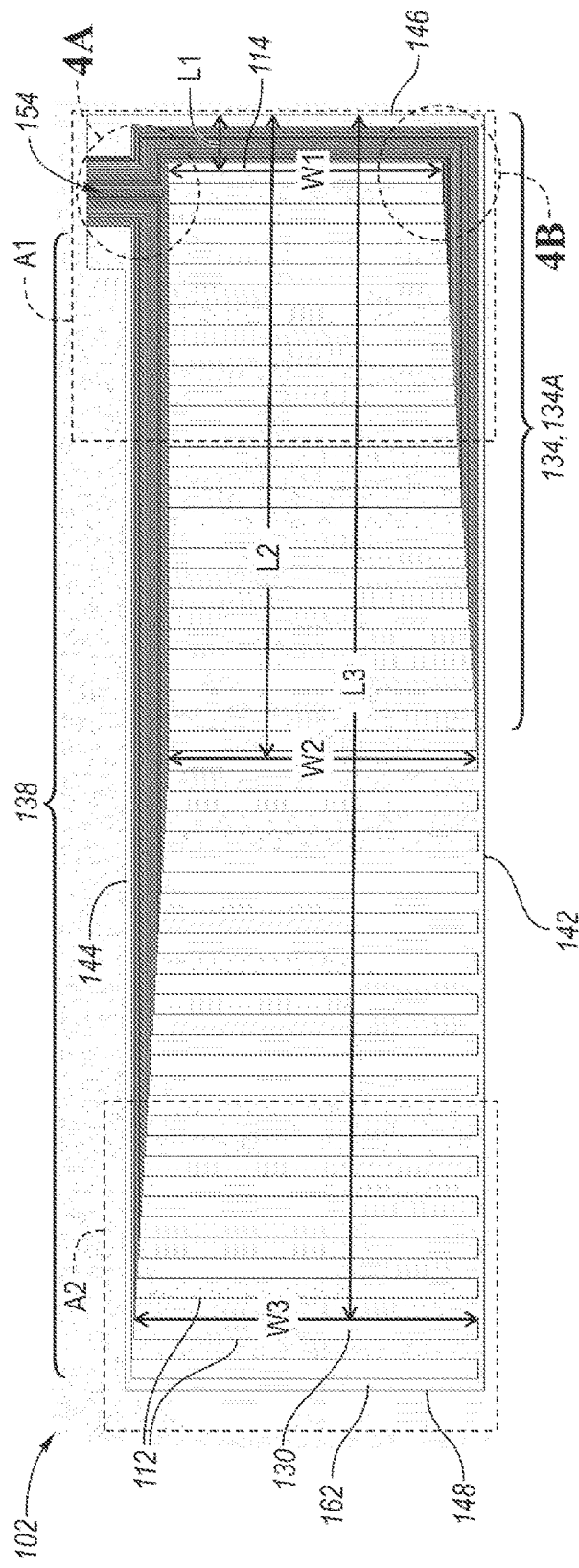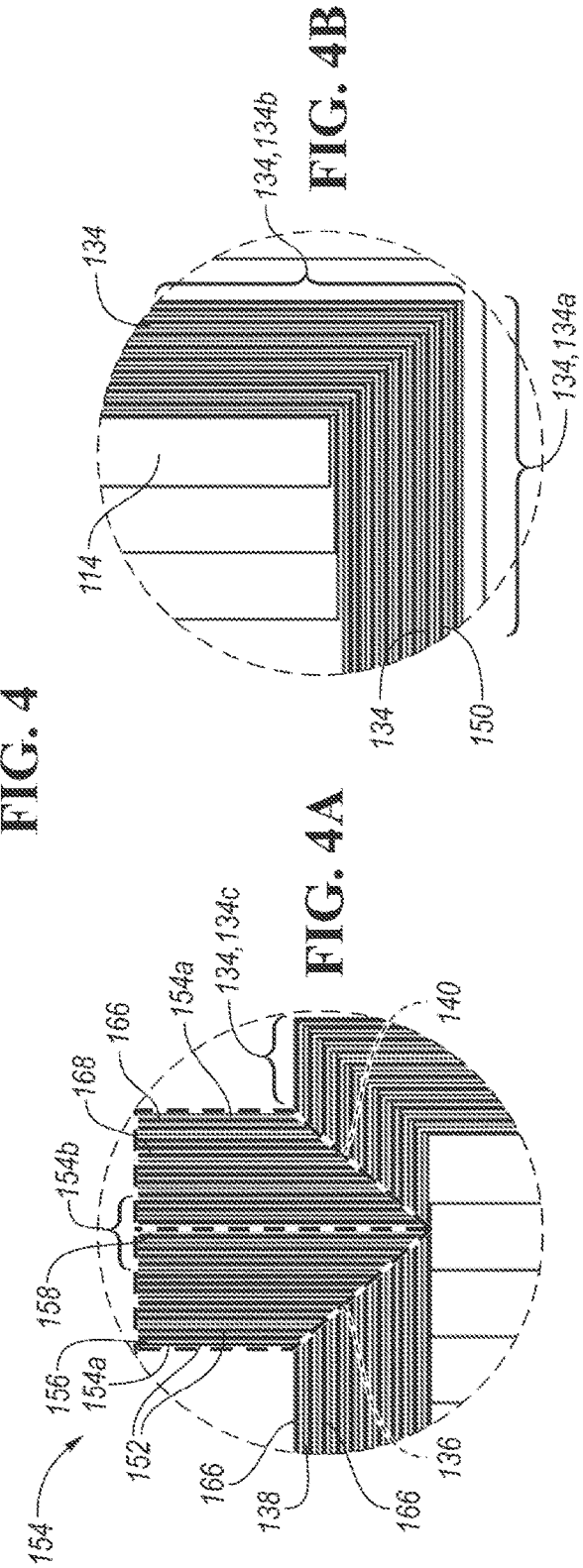
FIG. 4
FIG. 4A
FIG. 4B

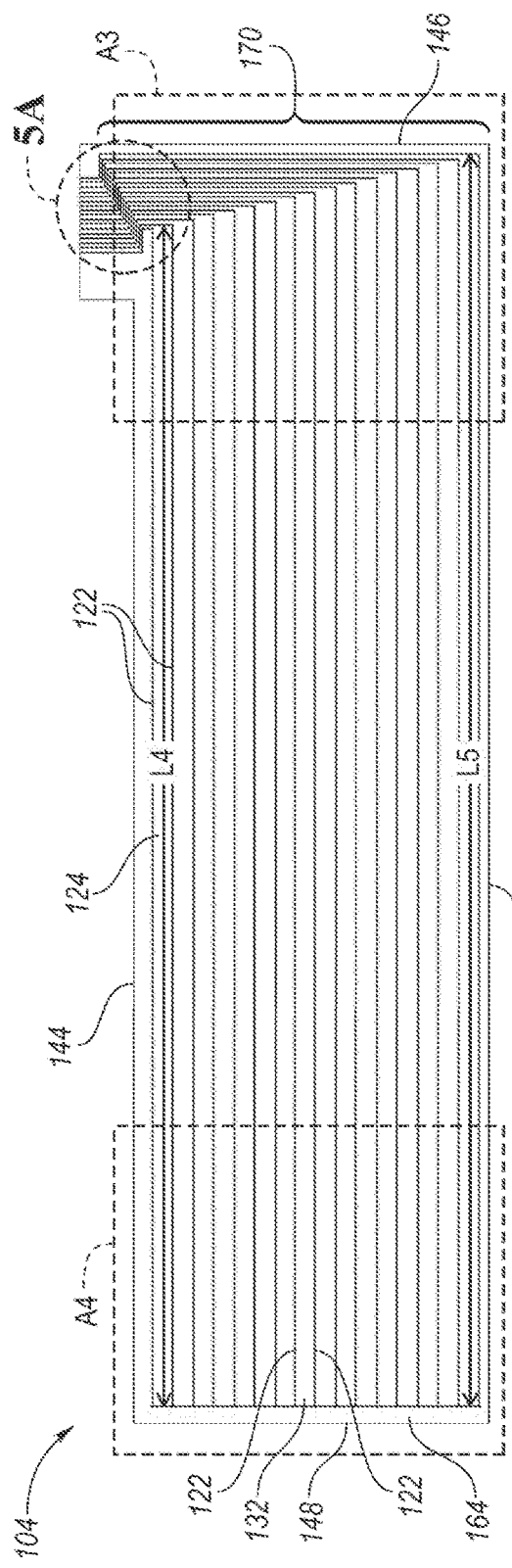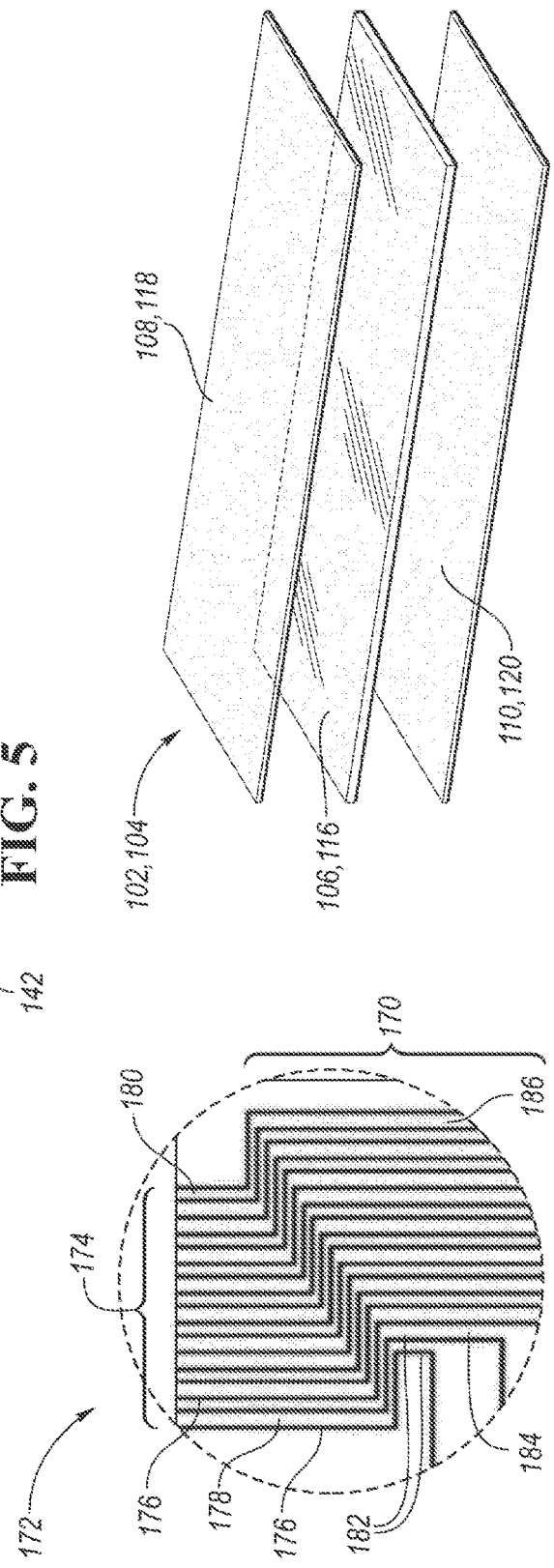

PRESSURE SENSING MAT

CROSS-REFERENCE TO RELATED APPLICATIONS

This application is the U.S. National Phase of PCT Application No. PCT/US2020/019486 filed on Feb. 24, 2020, which claims the benefit of U.S. Provisional Application Ser. No. 62/809,158 filed Feb. 22, 2019 the disclosures of which are hereby incorporated in their entirety by reference herein.

TECHNICAL FIELD

Aspects of the disclosure generally relate to a pressure sensing mat configured to aid in the prevention of pressure injuries, otherwise known as decubitus ulcers.

BACKGROUND

Pressure injuries, otherwise known as decubitus ulcers, pressure ulcers or bedsores, are lesions developed when a localized area of soft tissue of a subject is compressed between a bony prominence and an external surface for a prolonged time. Pressure injuries could appear in various areas of the body, such as elbows, knees, pelvis, lower back, and ankles. Development of pressure injuries are based on a combination of factors, such as, unrelieved pressure, friction, shearing forces, humidity, and temperature.

Patients lying in hospital beds and other surfaces often suffer from pressure injuries. Pressure injuries are a risk for patients in different hospital departments. For instance, pressure injuries may be in issue for patients lying on an operating table during an operation. Patients lying in hospital beds in other departments (e.g. intensive care unit, neo natal care unit, step down units, etc.) are also prone to pressure injuries. However, pressure injuries are not limited to hospitalized patients. Individuals confined to wheelchairs are prone to suffer from pressure injuries, especially in their pelvis, lower back, and ankles. Nursing and rehabilitation hope residents also can suffer from pressure injuries. Therefore, there is a relatively large number of settings within the hospital and in other environments where individuals may encounter problems with pressure injuries.

Although easily preventable or treatable if found early, if a pressure injury lingers, it becomes painful and treatment is both difficult and expensive. In many cases, pressure injuries can prove fatal, even under the auspices of medical care. According to one estimate, 2.5 million people suffer from pressure injuries in the United States each year, resulting in over 60,000 deaths annually. Pressure sensing mats have been utilized in hospital bed settings to aid in the prevention of pressure injuries. The pressure sensing mats use capacitive or resistive sensors to track the pressure exerted on different regions of the body of a patient lying in the hospital bed.

SUMMARY

According to one aspect of this disclosure, a pressure sensing mat is provided. The pressure sensing mat may include a first portion and a second portion. The first portion may include a first conductive layer and a first non-conductive layer that may be layered to the first conductive layer. The second portion may include a second conductive layer and a second non-conductive layer that may be layered to the second conductive layer. The first conductive layer may be continuous except for a plurality of discontinuities defining a plurality of conductive strips oriented in a first direction. The second conductive layer may be continuous except for a plurality of discontinuities defining a plurality of conductive strips oriented in a second direction. The pressure sensing mat may also include an insulative layer disposed between the first and second conductive layers. The pluralities of first and second conductive strips may form a conductive strip matrix having a plurality of capacitors. Each of the capacitors of the plurality of capacitors may be configured to provide a capacitance indicative of a pressure applied at each capacitor of the plurality of capacitors.

A pressure sensing mat system of the pressure sensing mat may include a non-transitory computer-readable medium having computer readable instructions stored thereon that is configured to be executed by a processor to receive capacitance data from the plurality of capacitors and determine capacitance based on the capacitance at each of the plurality of capacitors indicative of a pressure applied to the pressure sensing mat at each of its plurality of capacitors.

The first portion may include a first end and a second end. Each conductive strip of the first plurality of conductive strips may be formed as columns including a first column and a second column. The first column may have a first width and may be spaced apart from the first end by a first distance. The second column may have a second width that may be greater than the first width and may be spaced apart from the first end by a second distance, that may be greater than the first distance.

When the pressure sensing mat is used to detect a pressure of an individual, the first portion of the pressure sensor mat may be arranged to face towards the individual. The second end of the mat may be configured to be arranged beneath a head of the individual.

A number of columns may be disposed between the first column and the second column. A width of the first column and a width of the second column may differ. The width of each of the columns disposed between the first and second columns may increase monotonically from the first end to the second end.

The plurality of conductive strips of the first conductive layer may include a plurality of rows and the at least one conductive strip of the second conductive layer may include a plurality of columns. The plurality of rows and the plurality of columns may be arranged orthogonally to each other, and in other embodiments, in a non-parallel orientation with respect to each other.

The insulative layer may be comprised of a foam material.

The first non-conductive layer may be continuous except for a third plurality of discontinuities. The third plurality of discontinuities may correspond to the first plurality of discontinuities.

The first conductive layer may be disposed between the first non-conductive layer and the insulative layer.

The second non-conductive layer may be continuous except for a fourth plurality of discontinuities. The fourth plurality of discontinuities may correspond to the third plurality of discontinuities.

The second conductive layer may be disposed between the second non-conductive layer and the insulative layer.

According to another aspect of this disclosure, a pressure sensing mat is provided. The pressure sensing mat may include a first portion and a second portion. The first portion may include a first conductive layer that may be sandwiched between a first non-conductive layer and a non-conductive layer. The first non-conductive layer and the first conductive layer may define a first set of channels that may at least partially enclose a first conductive strip that may extend in a first direction. The second portion may include a second conductive layer that may be sandwiched between a third non-conductive layer and a fourth non-conductive layer. The third non-conductive layer and the second conductive layer may define a second set of channels that may at least partially enclose a second conductive strip that may extend in a second direction. The pressure sensing mat may include an insulative layer that may be disposed between the first portion and the second portion. The first conductive strip and the second conductive strip may form a capacitor that may be configured to provide a capacitance indicative of a pressure applied to the capacitor The first set of channels may at least partially enclose a third conductive strip and the second set of channels may at least partially enclose a fourth conductive strip. The third conductive strip and the fourth conductive strip may form a second capacitor that may be configured to provide a capacitance indicative of a pressure applied to the second capacitor. The first portion may include a first set of conductive leads.

The first portion may include a second set of conductive leads. The first conductive strip may be disposed in a left region of the first portion and the third conductive strip may be disposed in a right region of the first portion.

The first set of conductive leads may be disposed on a first side of the first portion and at least a portion of the second set of conductive leads may be disposed on a second side of the first portion, that may oppose the first side.

The first set of conductive leads may be formed by a third set of channels that may extend substantially in the second direction and may be defined by the first non-conductive layer and the first conductive layer.

The first set of conductive leads may be formed by a fourth set of channels that may extend in the first direction and may be defined by the first non-conductive layer and the first conductive layer.

The first set of conductive leads may be disposed in a connection region of the pressure sensor mat that may include a peripheral area and a medial area. The first set of conductive leads may include a first conductive lead and a second conductive lead. The first conductive lead may have a first length and may be disposed in the peripheral area. The second conductive lead may have a second length, that may be greater than the first length and may be disposed in the medial area.

The first set of conductive leads may include a number of conductive leads disposed between the first conductive lead and the second conductive lead. A length of the each of the conductive leads disposed between the first conductive lead and the second conductive lead may monotonically decrease from the peripheral area to the medial area.

The second set of conductive leads may include a first segment, a second segment, and a third segment. The first segment may be disposed on the second side of the first portion. The second segment may extend in the first direction from the first set of conductive leads. The third segment may extend from the second segment.

The first segment may be substantially orthogonal to the second segment.

At least one of the conductive leads of the first set of conductive leads may have a first width and the first conductive strip may have a second width that may be greater than the first width.

The first conductive layer may have a first surface area and the first non-conductive layer may have a second surface area and the second non-conductive layer may have a third surface area. The first surface area may be greater than the second and third surface areas.

The first portion may have a first thickness and the first set of channels may have a first depth that may be less than the first thickness.

The first and second non-conductive layers may be laminated to the conductive layer.

The first conductive layer may be formed of copper.

The first conductive layer may have a surface resistivity of at least 0.10 ohms.

According to another aspect of this disclosure, a method of making a pressure sensing mat is provided. The method may include providing a first laminated sheet including a first non-conductive layer, a second non-conductive layer, and a first conductive layer sandwiched therebetween, providing a second laminated sheet including a third non-conductive layer, a fourth non-conductive layer, and a second conductive layer sandwiched therebetween, removing portions of the first laminated sheet to define a first plurality of channels to form a first plurality of conductive strips extending in a first direction, removing portions of the second laminated sheet to define a second plurality of channels to form a second plurality of conductive strips extending in a second direction, attaching the first laminated layer to a first side of an insulative layer, and attaching the second laminated layer to a second side of the insulative layer.

The removing steps may each include etching the first and second laminated layers. As one example, the etching may be accomplished by applying a laser to metal the portions of the first and second laminated layers.

BRIEF DESCRIPTION OF THE DRAWINGS

FIGS. 4, 4A and 4B depict a top plan view and detailed view of a conductive layer, respectively, according to at least one embodiment.

FIGS. 5 and 5A depict a top plan view and detailed view of a conductive layer, respectively, according to at least one embodiment.

FIG. 6 depicts an exploded view of the conductive layer according to at least one embodiment.

DETAILED DESCRIPTION

Figure 1:
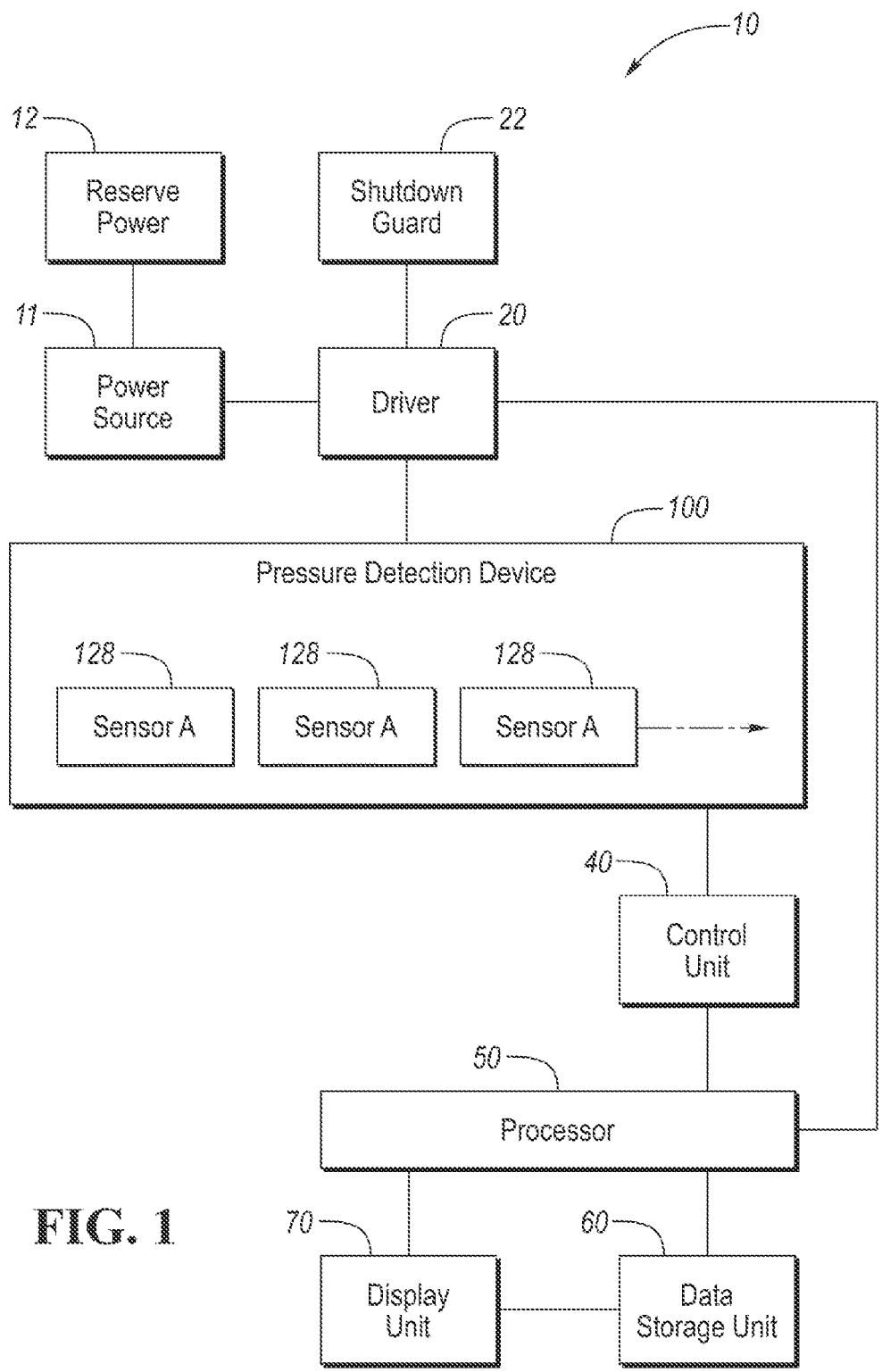
FIG. 1 is a schematic of the main components of a pressure sensing mat and related components to at least one embodiment.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

As used in the specification and the appended claims, the singular form "a," "an," and "the" comprise plural referents unless the context clearly indicates otherwise. For example, reference to a component in the singular is intended to comprise a plurality of components.

The term "substantially" or "about" may be used herein to describe disclosed or claimed embodiments. The term "substantially" or "about" may modify a value or relative characteristic disclosed or claimed in the present disclosure. In such instances, "substantially" or "about" may signify that the value or relative characteristic it modifies is within ±0%, 0.1%, 0.5%, 1%, 2%, 3%, 4%, 5% or 10% of the value or relative characteristic.

Aspects of the disclosure generally relate to a capacitive pressure sensing mat configured to aid in the prevention of pressure injuries. Other capacitive pressure sensing mats have been proposed. In one previous implementation, the pressure mat is composed of a matrix of knitted conductive fabric spaced apart by an insulator and connected by a woven ribbon to form a plurality of electrical capacitors. The knitted conductive fabric matrix is produced by standard processes associated with textile manufacturing. The material and manufacturing processes for these knitted conductive fabric pressure sensing mats may be costly thus requiring them to be reused several times to make their use economically feasible. Reusing the pressure mat may require the mat to be cleaned and sanitized after each use and may create sanitation issues of the mat is not sufficiently cleaned or sanitized between patients. Also, these knitted conductive fabric pressure sensing mats need to be specially designed and manufactured for different operating environments, e.g. intensive care units, operating rooms, nursing homes, wheelchairs. Therefore, in some instances, these pressure sensing mats do not provide a modular solution.

Pressure mats composed of knitted fabric may require individual calibration for accuracy and precision. Knitted fabrics include conductive threads or yarns that are relatively elastic and deformable. Available pressure mats are calibrated before use. During the calibration process, the capacitance of each sensor in the matrix is measured for one or more known pressures. The functional relationship between the known pressures and measured capacitance at each sensor is used to calibrate each sensor. Geometrical tolerances of knitted fabrics may have a relatively large range e.g., 0.5 mm to 1.5 mm, thereby adding variability to the capacitance measurements.

The capacitive pressure sensing mat of the present disclosure may be formed of spaced apart laminated conductive sheets. The geometrical tolerances of the laminated conductive sheets may have relatively smaller range e.g., 0.5 microns to 2 microns, than the knitted fabric matrix. Because the laminated conductive sheets have a narrower tolerance band as compared to pressure mats composed of knitted fabrics, calibration may be streamlined relative to sensing mats composed of knitted fabrics. In some instances, the use of laminated conductive sheets may obviate the need to calibrate every pressure mat before each pressure mat is used. As one example, a statistical analysis for a predetermined number of pressure mats may be used to determine the required frequency of calibrating the pressure mats composed of laminated conductive sheets. Decreasing the frequency and quantity of calibration processes may create efficiencies in manufacturing and may reduce costs.

One or more of the capacitive pressure sensing mats of the present disclosure may include relatively inelastic material such laminated conductive sheets that may mitigate relative movement between two or more layers and two or more sensors of the sheet as compared to known pressure mats composed of knitted fabrics. The knitted fabrics over time may begin to elongate and such elongation may reduce the useful life of the pressure mat. The relatively inelastic material of the pressure mat of the present disclosure may last longer by avoiding this potential issue.

Available pressure sensing mats are typically plugged into a power source and connected to a computer or controller to collect the measured data. One or more of the capacitive pressure sensing mats of the present disclosure may be configured for wireless power and communication. The capacitive pressure sensing mats of the present disclosure may be capable of communicating with a wireless network and powered by a rechargeable battery. The capacitive pressure sensing mats of the present disclosure may be configured to be disposable for use in the operating room. The pressure sensing mats of the present disclosure may be adaptable to a modular manufacturing method where the laminated sheet material may be cut to different sizes from the same stock material so that the laminated conductive sheets can be applied to many different use cases and settings. The pressure sensing mats disclosed in embodiments of the present disclosure provides one or more technical solutions to one or more of the technical drawbacks of the currently proposed pressure sensing mat.

Referring generally to the figures, a pressure sensing mat 100 is provided. The pressure sensing mat 100 may include a first portion 102 and a second portion 104. An insulative layer 126 may be disposed between the first portion 102 and the second portion 104. As shown in FIG. 6, the first portion 102 may include a first conductive layer 106 that may be sandwiched between a first non-conductive layer 108 and a second non-conductive layer 110. The first non-conductive layer 108 and the first conductive layer 106 may define a first set of channels 112. The first set of channels 112 may at least partially enclose a first conductive strip 114. As shown in FIG. 6, the second portion 104 may include a second conductive layer 116 that may be sandwiched between a third non-conductive layer 118 and a fourth non-conductive layer 120. The second conductive layer 116 and the third non-conductive layer 118 may define a second set of channels 122 that may at least partially enclose a second conductive strip 124 that may extend in a second direction. With the exception of the channels 112, 122, the first conductive layer 106 and the second conductive layer 116, respectively, may be continuous. The first conductive strip 114 and the second conductive strip 124 may form a matrix of capacitors (e.g. a capacitor 128 that may be configured to measure capacitance indicative of a pressure applied to the capacitor 128).

The first set of channels 112 may at least partially enclose a third conductive strip 130 and the second set of channels 122 may at least partially enclose a fourth conductive strip 132. The third conductive strip 130 and the fourth conductive strip 132 may form another capacitor 128. As one example, the first conductive strip 114 may be disposed within a left-side region of the first portion 102 and the third conductive strip 130 may be disposed in a right-side region of the first portion, when viewing the first conductive layer 106 in FIG. 6.

The first portion 102 may include a first set of conductive leads 134 and a second set of conductive leads 138. The first set of conductive leads 134 includes first conductive portions 140 and the second set of conductive leads 138 includes first conductive portions 136. The driver 20 (as shown in FIG. 1) is configured to supply voltage to the capacitors 128 through the first and second set of conductive leads 134 and 138. The processor 50 (as shown in FIG. 1) may be configured to measure the potential across the capacitors 128, calculate impedance values for each capacitor 128, and store the data in a data storage unit 60.

The pressure sensor mat may include a first side 142, a second side 144, opposing the first side 142, a first end 146, and a second end 148. The first end 146 and the second end 148 may extend between the first and second sides 142, 144. The first set of conductive leads 134 may be disposed on the first side 142 of the first portion 102. At least a portion of the second set of conductive leads 138 may be disposed on the second side 144 of the first portion 102. The first set of conductive leads 134 may be formed by a third set of channels 150 defined by the first conductive layer 106 and at least one of the first non-conductive layer 108 or the second non-conductive layer 110 that may extend in a direction parallel to the first side 142, or second side 144, or both. The first set of conductive leads 134 may be formed by a fourth set of channels 152 that may extend in a direction that is parallel the first end 146, second end 148, or both.

As shown in FIG. 4A, the pressure sensing mat 100 may include a connection region 154 that may be configured to engage or be connected with a connector (not illustrated). The connection region 154 may include a peripheral region 154a and a medial region 154b. The first set of conductive leads 136 may include a first conductive lead 156, disposed in the peripheral region 154a, and a second conductive lead 158 that may be disposed in the medial region 154b. The first conductive lead 156 may be shorter than the second conductive lead 158. A number of conductive leads may be disposed between the first conductive lead 156 and the second conductive lead 158. A length of each of these additional conductive leads may monotonically decrease from the peripheral region 154a to the medial region 154b.

As shown in FIG. 4B, the second set of conductive leads 134 may include a first segment 134a, that may be disposed on the first side 142 of the first portion 102, a second segment 134b, and a second segment 134c. The second segment 134b may extend in the first direction from the first segment 134a to the third segment 134c. The third segment 138c may extend between the second set of conductive leads 140 and the second segment 134b. As one example, the first segment 134a may be positioned substantially orthogonal to the second segment 134b. The conductive leads 134, 138, or the first conductive portions 136, 140, or both, may each have a width that is greater than a width of one or more of the conductive strips 114, 124, 130, 132.

In one or more embodiments, the conductive strips 114, 130 of the first conductive layer 106 may be formed by columns and the conductive strips 124, 132 of the second conductive layer 116 may be formed by rows. A width or a distance of each of the columns or conductive strips disposed between the conductive strips 114, 130 may differ. As one example, the width of each of the columns or conductive strips disposed between the conductive strips 114, 130 may monotonically increase between the first end 146 and the second end 148. When the pressure sensing mat 100 is used to detect pressure applied by an individual, the first portion 102 may be arranged to face towards the occupant. As one example, the second end 148 may be arranged beneath the head area or beneath the head and neck area of the individual. Because an individual's head and neck area may move e.g., tilt up, slide side-to-side, or roll, relatively more than the rest of an occupant's body, the larger conductive strips disposed near the second end 148 may provide better resolution than the smaller conductive strips disposed near the first end 146.

Reference is now made to the block diagram of FIG. 1, showing an embodiment of a pressure sensing may system 10. The system 10 may include at least one pressure sensing mat 100 including a plurality of sensors such as capacitors 128, a driver 20, a control unit 40 which may be connected to a power source 11, a processor 50, a data storage unit 60 and a display unit 70. Power may be supplied via a power cord connected to a wall outlet, or via battery power, optionally rechargeable. Battery support also allows for movement of the bed without requiring a powering off of the system 10. As a safety measure and for compliance tracking, caregiver authentication may be required via a shutdown guard 22 to confirm powering off of the control unit 40, such as with entry of a caregiver's employee identification number. While the system identified in FIG. 1 is a capacitive sensor system, in other embodiments, other methods can be utilized, such as resistive or piezoresistive systems.

The capacitors 128 may be arranged at different locations on the pressure sensing mat 100. In an example, the capacitors 128 may be arranged in a two-dimensional grid across the surface of the pressure sensor mat 100. The driver 20 may be configured to supply voltage to the capacitors 128 in the pressure sensing mat 100, and the processor 50 may measure the potential across the capacitors 128, calculate impedance values for each capacitor 128, and store the data in a data storage unit 60. The stored data may be further processed, analyzed, and displayed on the display unit 70, such as a computer screen, laptop, personal digital assistant (PDA), tablet device, mobile phone screen, printed sheet, or integrated display screen. Although presented in the block diagram of FIG. 1 as separate blocks, the system 10 may optionally be integrated into a stand-alone system.

Figure 2:
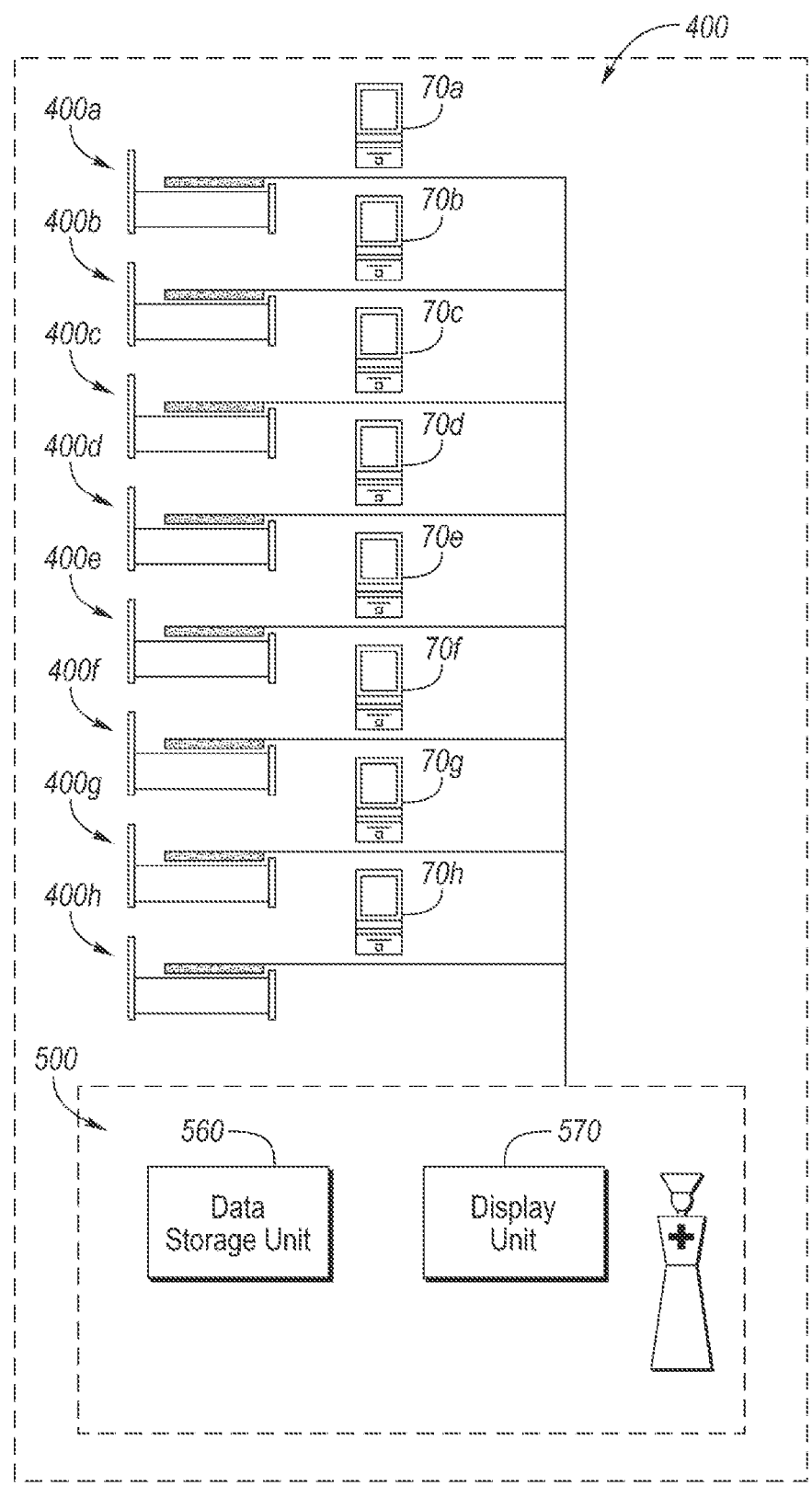
FIG. 2 is a schematic of an individual care environment according to at least one embodiment.

Referring now to FIG. 2, an individual care environment 400 may include a number of sub-systems 400a through 400h in communication with a common remote-control center 500. The individual care environment 400 may be in a hospital, nursing home, home care or rehabilitative care environment, as examples. If the individual care environment 400 is a hospital, the common remote-control center 500 may be a nursing station. As shown in FIG. 1, each of the sub-systems 400a-400h includes a bed. The sub-systems 400a through 400h may be configured to communicate with the common remote-control center 500, for example at a nursing station. This communication can be provided via wiring to a nurse call system, or alternatively via wireless communication (e.g., BLUETOOTH, ZIGBEE, Wi-Fi, cellular, etc.) to the nursing station. Alternatively, the sub-systems 400a-400h may be located remotely from one another, for example each in an individual home, and the remote-control center 500 may be a manned observation station.

Figure 3A:
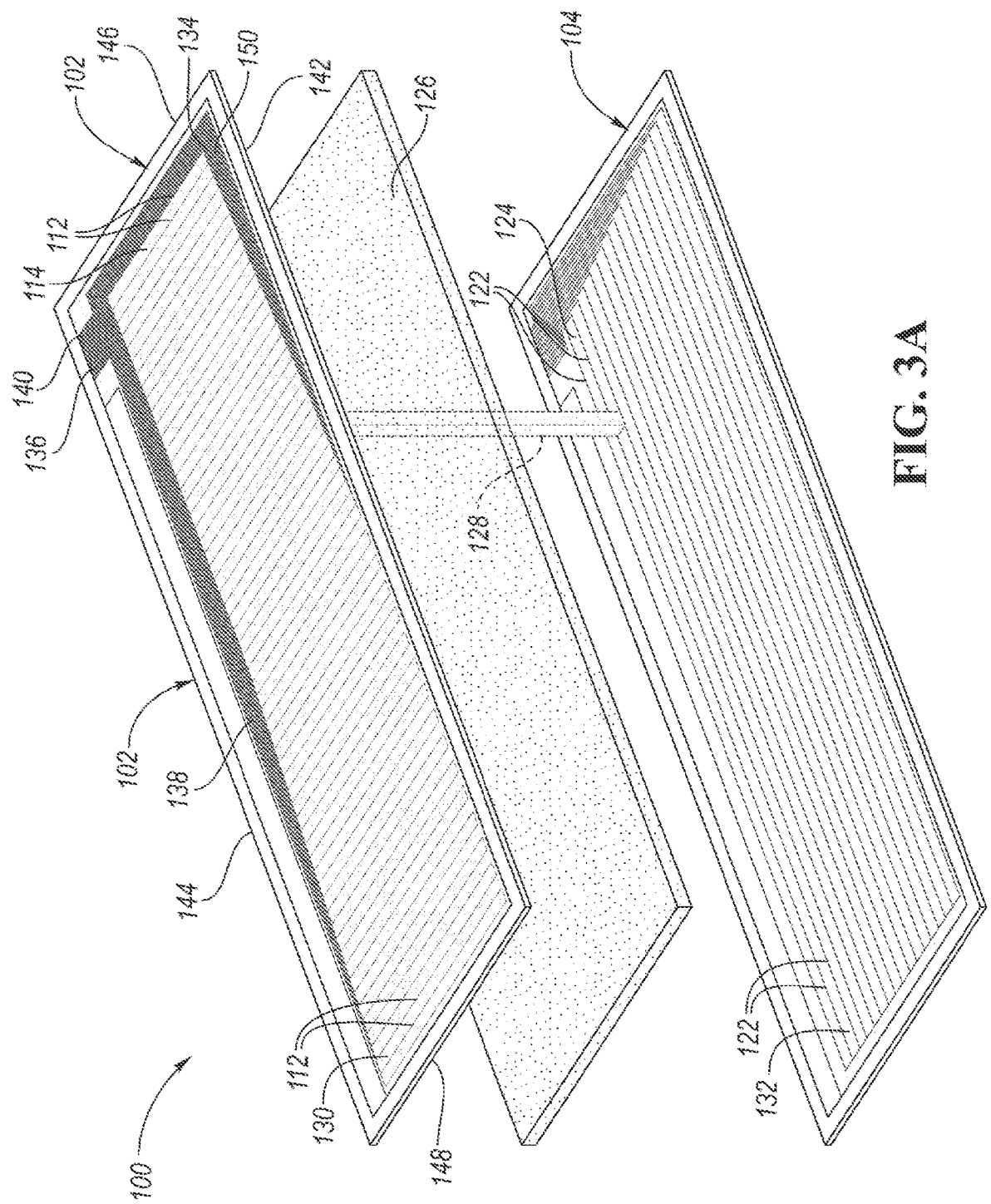
FIGS. 3A and 3B depict a fragmented, exploded, perspective views of multiple embodiments of pressure sensing mats.

FIG. 3A illustrates a perspective view of a portion of the pressure sensing mat 100. The first portion 102 is positioned above the second portion 104 and the insulative layer 126. As one example, the first portion 102, the second portion 104, and the insulative layer 126 may be elongated and rectangular. The first portion 102 may include the first set of channels 112 that may at least partially enclose the first conductive strip 114. The second portion 104 may include the second set of channels 122 that may at least partially enclose a second conductive strip 124. The first conductive strip 114 may extend in the first direction, such as side-to-side, and the second conductive strip 124 may extend in the second direction, such as end-to-end. The dashed lines extending between the first portion 104 and the second portion 104 may represent a capacitor 128. While one capacitor 128 is shown, a number of capacitors are formed at each point of intersection between the conductive strips in the first portion 102 and the conductive strips in the second portion 104.

As one example, the insulative layer 126 may be formed by a non-conductive material. In other words, the material of the insulative layer 126 may not allow a flow of charge such as electrical current through or across the insulative layer 126. The non-conductive material may be film comprised of a thermoplastic polyurethane (TPU), polyethylene terephthalate (PET), foam or other suitable material.

The first portion 102 and the second portion 104 may each be mechanically attached to the insulative layer 126 by an adhesive. As one example, a double-sided tape (DST) may be laid along either the insulative layer 126 or the first portion 102, the second portion 104, or both. The insulative layer 126 may then be laid on to the first and second portion 102, 104 and vice-versa.

Figure 3B:
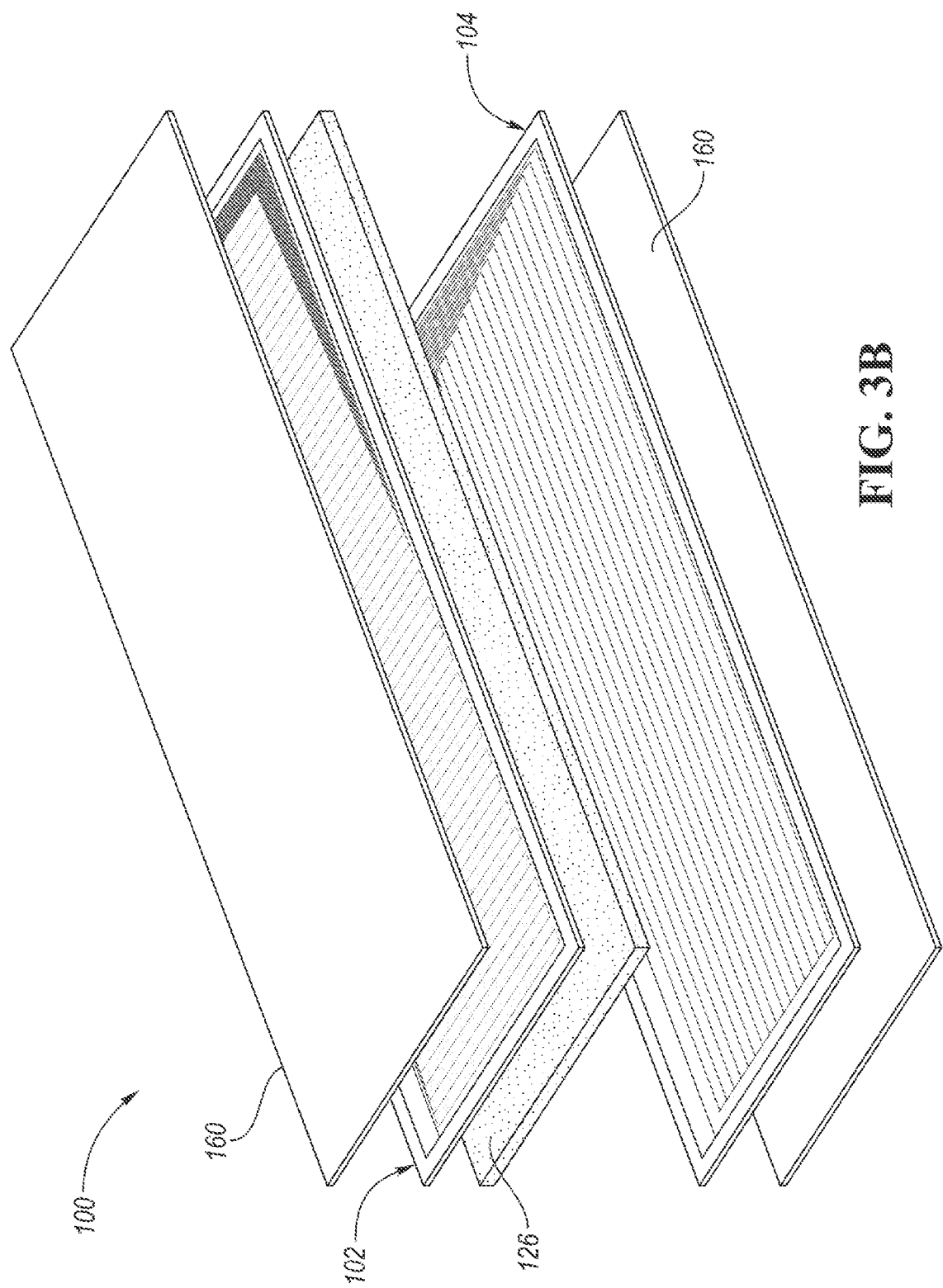

FIG. 3B illustrates the pressure sensing mat 100 according to one or more embodiments. As one example, the pressure sensing mat 100 may include one or more covers 160 that may be fixed directly to either the first portion 102 or the second portion 104, or both. The cover 160 may be fixed to the first and second portions 102, 104 by an adhesive such as double-sided tape (DST), liquid adhesive e.g. glue that may be applied as a spray or a number of beads. The adhesive may be applied to outer portions of the cover 160 or the first and second portions 102, 104 or to inner portions of the same.

The covers 160 may be formed of a fabric or a polymeric material. As one example, the material of the covers 160 may be formed of a water-resistant material that is configured to prevent a liquid from penetrating through the cover 160 to the first and second portions 102, 104. If water or other liquid penetrates the cover 160, the liquid may cause a short of one or more of the capacitors 128. As one example, the cover 160 may be composed of polytetrafluoroethylene (PTFE) or expanded PTFE. A water-resistant cover 160 may be useful when the pressure sensing mat 100 is used by burn patients or within an operating room environment where liquids from the patient's body or otherwise may be deposited on the cover 160.

As another example, one or more of the covers 160 may extend the longevity of the pressure sensing mat 100.

FIG. 4 illustrates a top view of the first conductive layer 106. The first conductive layer 106 may define the first set of channels 112 that may enclose the first conductive strip 114 and the third conductive strip 130. The first set of channels 112 are depicted by the black lines disposed on either side and the ends of the conductive strips 130, 114. The first conductive strip 114 may have a width W1 and the third conductive strip 130 may have a width W3 that may be greater than the first width. At least one of the conductive strips disposed between the first conductive strip 114 and the third conductive strip 130 may have a width W2. The second width W2 may be less than the third width W3 and greater than the first width W1. The first conductive strip 114 may be spaced apart from the first end 146 by a first distance L1, one of the conductive strips disposed between the first and third conductive strips 114, 130 may be spaced apart by a second distance L2, and the second conductive strip 124 may be spaced apart from the first end 146 by a third distance L3. The third distance L3 and the second distance L2 may each be greater than the first distance L1.

The first conductive layer 106 may include a right region A1 and a left-region A2, as represented by dashed lines on the left side and right side of FIG. 4. As mentioned above, the left-region A2 may include wider conductive strips than conductive strips within the right-region A1. As such, the left-region A2 may be positioned beneath the occupant's head or neck region.

FIG. 4A illustrates a detailed view of the connecting region 154 of the first portion 102. The connecting region 154 includes a first conductive portions 136, 140. The first conductive portions 136, 140 may include the peripheral portions 154a and a medial portion 154b disposed therebetween. The first conductive lead 156 may be disposed near the peripheral portion 154a and the second conductive lead 158 may be disposed near the medial portion 154b. The conductive leads 156, 158 and a number of other conductive leads of the first conductive portions 140 are depicted as the white lines arranged vertically and disposed between channels of the fourth set of channels 152, depicted as black lines adjacent to the vertical white lines. The first conductive portions 140 may be formed by a sixth set of channels 168 depicted as vertical black lines disposed in within the dashed lines enclosing the first conductive portions 140.

The fifth set of channels 166 and the second set of conductive leads 138 may extend between the first conductive portions 136 and a number of the conductive strips. As an example, the outermost channels of the fifth set of channels 166 may extend to the conductive strip that is positioned furthermost from the connection region 154. And the innermost channels of the fifth set of channels 166 may extend to the conductive strip positioned at a medial portion of the first portion 102, such as the conductive strip on the line W2.

The third segment 134c of first set of conductive leads 134 may extend between the first conductive portions 140 and the second segment 134b of the first set of conductive leads 134. The channels, represented by the black lines, and the conductive leads 134 of the third segment 134c may be positioned orthogonally with respect the channels of the second segment 134b of the conductive leads 134. As an example, the channels and the conductive leads 134 of the first segment 134c positioned near a periphery of the pressure sensing mat 100 may have the same length as the channels of conductive leads 134 of the first segment 134c positioned closer to the conductive strips.

The outer most channels and conductive leads of the third segment 134c of first set of conductive leads 134 may extend to a conductive strip disposed towards a medial portion of the first portion 102, such as the conductive strip to the right of the line W2. And the innermost channels and conductive leads of the third segment 134c of first set of conductive leads 134 may extend to a conductive strip positioned closest to the first end 146, such as the first conductive strip 114.

FIG. 4B illustrates a detailed view of portions of the first set of conductive leads 134. The first segment 134a of the first conductive leads may extend along and may be disposed between the first side 142 and the conductive strips. The second segment 134b may extend between the third segment 134c and the first segment 134a.

FIG. 5 illustrates a top plan view of the second portion 104. The second portion may include a right region A3 and a left region A4. The right region A3 may be disposed below or above the right region A1 of the first portion 102 and the left region A4 may be disposed below or above the left region A1.

The second portion 104 may include the second set of channels 122 that may enclose the conductive strips of the second portion 104. Each of the conductive strips may extend between a channel disposed closest to the second end 148 and a third set of conductive leads 170. The conductive strip positioned closest to the second side 144, such as the second conductive strip 124, may have a length L4 and the conductive strip positioned closest to the first side 142 may have a length L5, which may be greater than the length L4.

FIG. 5A illustrates a detailed view taken along the lines 5A in FIG. 5. The second portion 104 may include a connector region 172 that may include a third set of conductive leads 174. Each of the conductive leads of the first set 174 may be formed by a seventh set of channels 176. The third set of conductive leads 174 may include a third conductive lead 178 and a fourth conductive lead 180. In one or more embodiments, the third conductive lead 178 may be connected to the second conductive strip 124 and the fourth conductive lead 180 may be connected to the conductive strip disposed closes to the first side 142. The fourth conductive lead 180 may have a length that is less than a length of the third conductive lead 178.

The third set of conductive leads 170 may be formed by an eighth set of channels 182 and may include a first conductive lead 184 and a second conductive lead 186. The first conductive lead 184 may be connected to the third conductive lead 178 and the second conductive lead 186 may be connected to the fourth conductive lead 180. The first conductive lead 184, the second conductive lead 186, and the conductive leads disposed therebetween may each include end portions that may be positioned substantially orthogonal to the third conductive lead 178, the fourth conductive lead 180, or both.

In one or more embodiments, the conductive leads 134, 138 and the conductive leads 136, 140, each of the first portion 102, may have a width that is less than a width of the conductive leads 170 and conductive leads 174 of the second portion 104.

During operation of the pressure sensing mat 100, voltage may be applied through the conductive leads 136, 140, 174 to the conductive leads 134, 138, 170, and to the conductive strips 112, 122, 130, 132. With the applied voltage, the capacitors 128 may be formed between the first portion 102 and the second portion 104. Capacitance measurements from each of the capacitors 128 may be made by processor 50 through one or more of the conductive strips 112, 122, 130, 132 to the adjoining conductive leads 134, 138, 170 and to the conductive leads 136, 140, 174.

FIG. 6 illustrates an exploded view of either the first portion 102 or the second portion 104 prior to forming (e.g., etching) the channels. The non-conductive layer 108, 118 positioned above the conductive layer 106, 116, may be layered and adhered to a top surface of the conductive layer 106, 116 and the non-conductive layer 110, 120 may be layered and adhered to a bottom surface of the conductive layer 106. The non-conductive layers 108, 110, 118, 120 may be permanently assembled to the conductive layer 106, 116 by applying heat, pressure, welding, adhesive, or some combination thereof.

In one or more embodiments, the non-conductive layers 108, 110, 118, 120 may be smaller than the conductive layer 106, 116. In other words, a surface area of the non-conductive layers 108, 110, 118, 120 may be smaller than a surface area of the conductive layer 106, 116. Because the non-conductive layers 108, 110, 118, 120 have a smaller surface area than the surface area of the conductive layer 106, 116, a portion of the conductive layer 106, 116 may be exposed.

The exposed portions may be referred to as a first bare bar 162 (FIG. 4) in the first portion 102 and a second bare bar 164 in the second portion 104 (FIG. 5). The first bare bar 162 and the second bare bar may be used to test one or more electrical properties of the first portion 102 and the second portion 104.

As an example, the electrical measurement devices may engage one or more of the bare bars 162, 164 to measure resistance, conductivity or other electric characteristic of the conductive layers 106, 116. The bare bars 162, 164 may be positioned near a periphery of the first and second portions 102, 104, respectively. Positioning the bare bars 162, 164 near the periphery may provide measurement points without disassembling the non-conductive layers 108, 110, 118, 120 from the conductive layers 106, 116.

Figure 7:
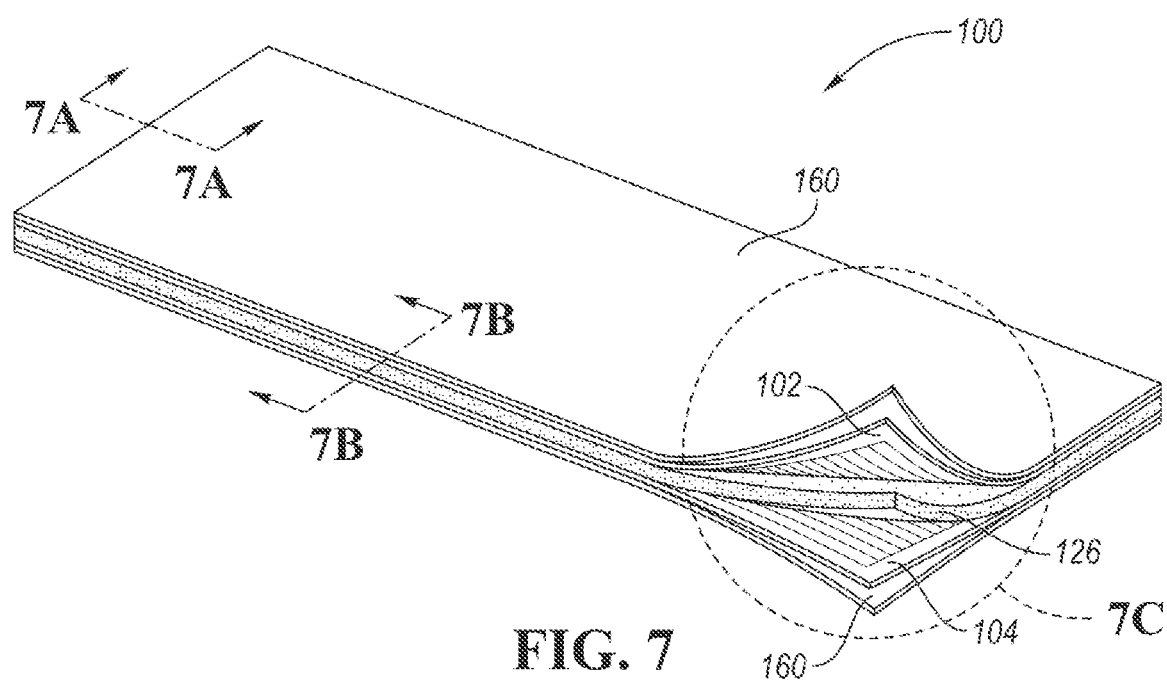
FIGS. 7, 7A, 7B and 7C depict a fragmented tear-away view, cross-sectional views, and a detailed view of the pressure sensor mat according to at least one embodiment.

FIG. 7 illustrates a partial-perspective view of the pressure sensing mat 100. To better portray the layers of the mat, a corner of the pressure sensing mat 100 is fanned out to show at least some of the layers of the pressure sending mat 100.

Figure 7C:
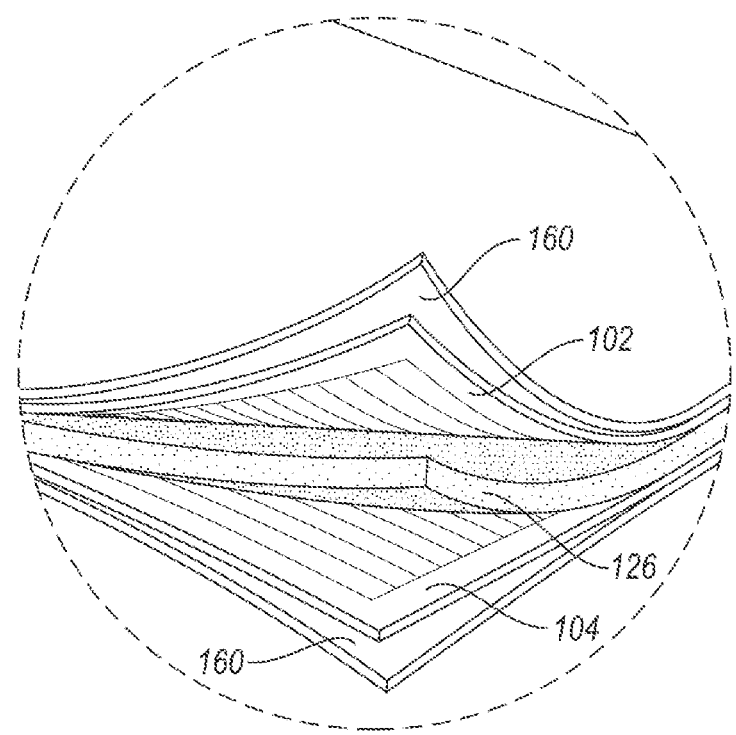
Figure 7A:
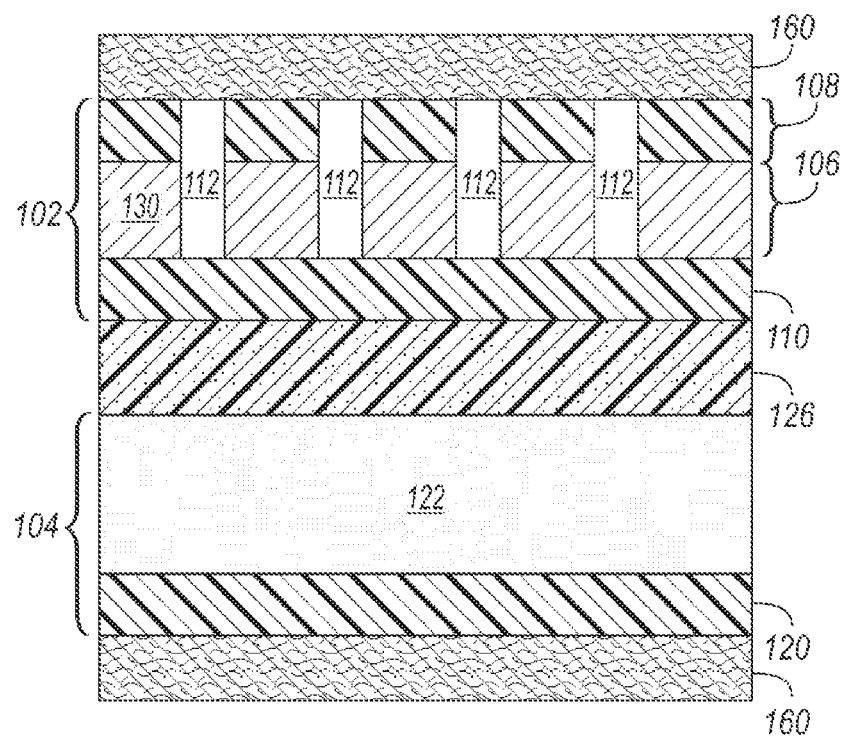
Figure 7B:
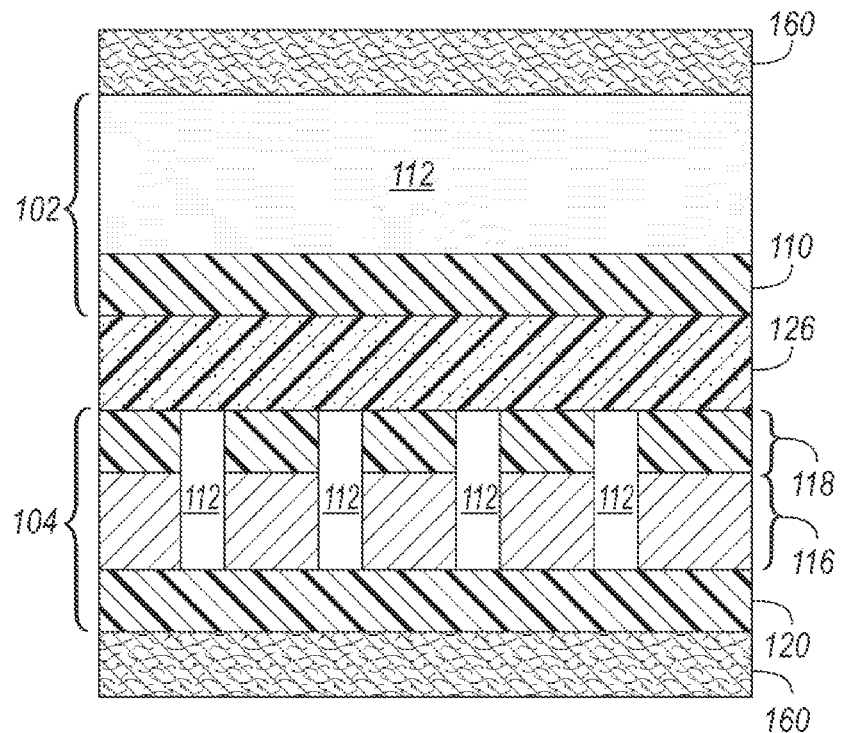

FIG. 7A illustrates a partial cross-sectional view of the pressure sensing mat 100 taken along the lines 7A in FIG. 7 and FIG. 7B illustrates a partial cross-sectional view of the pressure sensing mat 100 taken along the lines 7B in FIG. 7. FIG. 7A and FIG. 7B are each magnified to better illustrate the layers of the mat. As illustrated the covers 160 may each form the top and bottom surfaces of the mat. As previously mentioned, the covers 160 may not be used for all configurations of the mat 100. The covers 160 may lie along the first non-conductive layers 108 and the fourth non-conductive layer 120, respectively.

The first conductive layer 106 and the second conductive layer 116 may each be at least partially formed of a conductive metal or alloy material. As one example, the conductive layers 106, 116 may each be formed by a laminated copper material, such as 150 nm copper laminated. The laminated copper material may have a thickness ranging between 25 microns and 75 microns. As one example, Table 1 provides material properties of the 150 nm copper laminated material. In one or more embodiments, the conductive layers 106, 116 may each be formed of or include silver, aluminum, or other suitable conductive materials.

TABLE 1

| No | Criterion | Test method | Specification | Unit |
|---|---|---|---|---|
| 1 | Thickness | ISO4593 | 49 ± 8 | μ |
| 2 | Tensile Strength | ASTM D-882 | MD: 80 ± 52 TD: 70 ± 52 | N |
| 3 | Puncture Resistance | FTMS 101C 2065 | >40 | N |
| 4 | Lamination strength | ASTM D-882 | >300 | gr/Inch |
| 5 | Metal adhesion | Tape test with 3M 610 tape, HCTP 13 | No metal removal | |
| 6 | Copper thickness | | 150 ± 40 | nm |
| 7 | Surface Resistivity | | 0.07-0.21 | Ω/m |

The first and second non-conductive layers 108, 110 may be laminated to the first conductive layer 106 and the third and fourth non-conductive layers 118, 120 may be laminated to the second conductive layer 116. As an example, the conductive layers 106, 116 may be coated by a non-conductive film. As another example, the non-conductive layers 108, 110, 118, 120 may each be composed of a plastic or polymeric material such as a thermoplastic polyurethane (TPU), or polyethylene terephthalate (PET), or some combination thereof. One or more of the non-conductive layers 108, 110, 118, 120 may have a thickness that is approximately half of the thickness of the copper material. For example, the copper material may have a thickness of 49 microns while the thickness of the non-conducive layers 108, 110, 118, 120 may have thickness of 23 microns.

The thickness of the non-conductive layers 108, 110, 118, 120 may be increased to provide a number of advantages. As an example, increasing the thickness of the non-conductive layers 108, 110, 118, 120 may prevent tearing or cracking of the conductive layers 106, 116, to increase the durability and the useful life of the mat 100. As another example, the non-conductive layers 108, 110, 118, 120 having a thickness in the range mentioned above may prevent or reduce noise associated with the copper material moving as the occupant moves along the mat. Much like a bag of chips or other food packaged in a metallic foil, the conductive layers 106, 116, without the non-conductive layers tend to generate noise as the occupant moves on the mat. This noise may be an annoyance for the patient or another positioned near the mat. One or more of the non-conductive layers 108, 110, 118, 120 may mitigate this noise.

The insulative layer 126 may be sandwiched between the first portion 102 and the second portion 104 and may have a thickness that may be exponentially greater than the thickness of the first or second portions 102, 104. As an example, the insulative layer 126 may have a thickness that ranges between 1.0 mm to 7 mm.

Each of the channels 112, 122 may have a width ranging between 0.05 mm and 5 mm. As the width of the channels increases, the size of pixels may increase. In one or more embodiments, the channels 112, 122 may extend through at least one of the non-conductive layers 108, 110, 118, 120 of each portion 102, 104 and through the conductive layers 106, 116. In one or more embodiments, the surface defining the channels 112 may lie along the insulative layer 126 instead of being layered with the uppermost cover 160. Such a position may provide a waterproof or at least a water-resistant barrier between the outermost portions of the matt 100 and the conductive layer 106.

While the cross-sectional views of FIGS. 7A and 7B only illustrate the first set of channels 112 that form the third conductive strip 130 and the second set of channels 122 the form the fourth conductive strip 132, the configurations illustrated equally apply to the other channels that form the sets of signal detecting leads, signal receiving leads, and other conductive strips.

The channels 112, 122 may be formed by a laser etching process. The process may include providing and extending the laminated conductive material along a work surface. The laminated conductive material may be pre-cut to a predetermined size and shape or the laminated material may be a portion of a coil of the laminated conductive material. The laminated conductive material may be fixtured or held in place by a number of vacuums disposed along the work surface. The suction devices may be configured to apply a predetermined pressure of vacuum so that the laminated conductive material is held relatively flat across the work surface. One or more lasers may then be applied to remove or etch the laminated conductive material to form the channels. As another example, one of the lasers may cut portions of the laminated conductive material from the coil or cut peripheral portions of the material to a required length and width.

The width, length, position and depth of the channels may be measured by a coordinate measuring machine or other suitable measurement device. As another example, electrical resistance across a number of sections or an entirety of a test sample of one of the portions 102, 104 may be measured. The measured electrical resistance of the tested sample may be compared to a master sample having a known electrical resistance. The resistance measurement device may be attached to a portion of the conductive layer 106, 116 that is not covered or laminated by non-conductive layers 108, 110, 118, 120.

As an example, the laser be a fiber laser system a $CO_2$ laser system, or another suitable laser system. The laser beam may move across the laminated conductive material between two or more known reference coordinates at a number of velocities. As the beam of the laser approaches a predetermined position requiring a change in direction, the velocity of the laser may be decreased. However, as the velocity of the laser decreases, a number of adjustments may be required including but not limited to the power or focal point of the laser.

FIG. 7C illustrates a detailed view of a portion of the pressure sensing mat. The top and bottom covers 160 are shown as curled away from the first portion 102 and the second portion 104. The first portion 102 and the second portion 104 are each shown as curled away from the insulative layer 126. For purposes of clarity, the non-conductive layers 108, 110, 118, 120 are not shown curled away from the conductive layers 106, 116.

Figure 8:
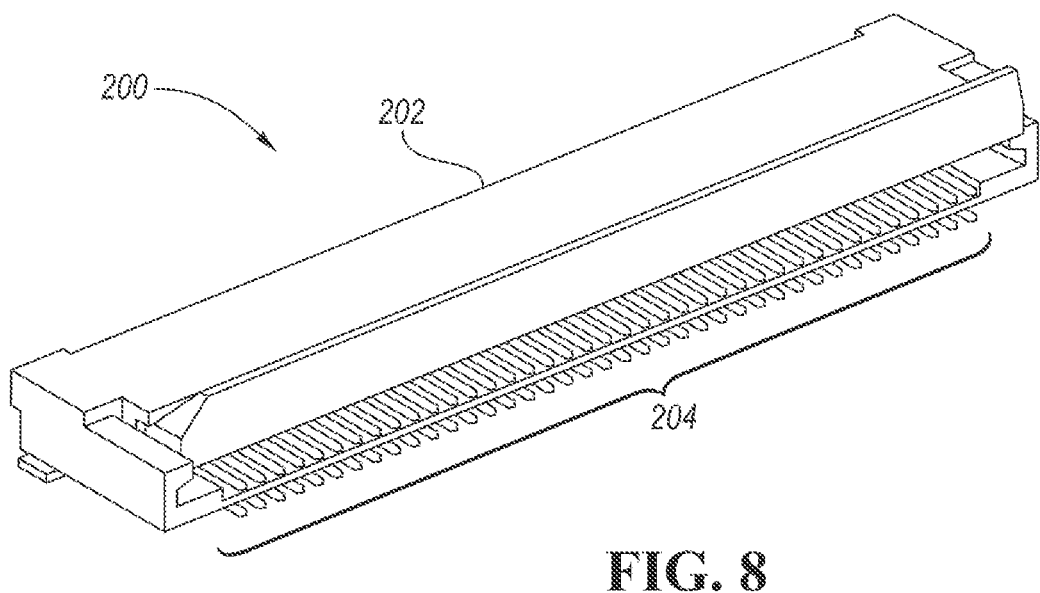
FIG. 8 depicts a perspective view of an exemplary connector.

FIG. 8 illustrates a perspective view of an exemplary connector. As one example, the connector may be a flat flex connector 202. The connector 202 may include a housing 204 and a number of connector leads that may be fixed to the signal receiving leads of the first and second portions 102, 104.

Figure 9:
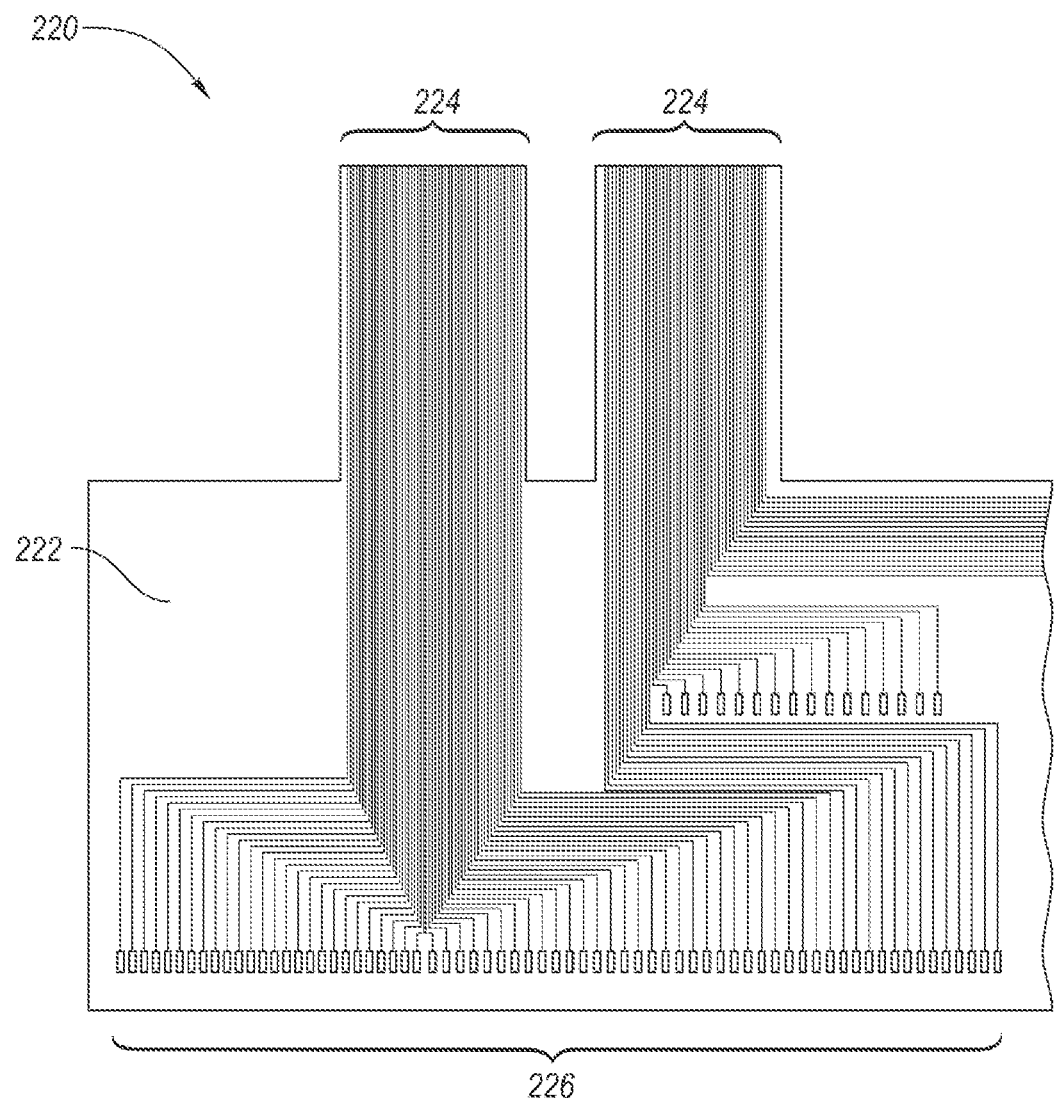
FIG. 9 depicts a perspective view of another connector.

FIG. 9 illustrates a perspective view of another exemplary connector. As one example the connector may be a flexible printed circuit connector 220. The connector 220 may include a number of leads 224 that may be disposed on a substrate 222. The leads may include a number of connection points 226 that may be fixed to the signal receiving leads of the first and second portions 102, 104.

The connectors 202, 220 may each be provided with a communications device such as a transmitter that may be connected and configured to communicate the data to the remote-control center 500 (FIG. 2). This communication can be provided via wiring or alternatively via wireless communication (e.g., BLUETOOTH, ZIGBEE, Wi-Fi, cellular, etc.).

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A pressure sensing mat comprising:
  a first portion including a first conductive layer contacting a first non-conductive layer, wherein the first conductive layer and the first non-conductive layer define a first set of channels defining a first plurality of conductive strips oriented in a first direction, wherein the first portion includes first and second sides, wherein the first set of channels extend to the first and second sides;
  a second portion including a second conductive layer layered to a second non-conductive layer, wherein the second conductive layer includes a second plurality of discontinuities defining a second plurality of conductive strips oriented in a second direction; and an insulative layer disposed between the first portion and the second portion, wherein the first plurality of conductive strips and the second plurality of conductive strips form a conductive strip matrix having a plurality of capacitors configured to provide capacitances indicative of pressures applied at capacitors of the plurality of capacitors.

2. The pressure sensing mat of claim 1, wherein when the pressure sensing mat is used to detect a pressure of an individual, the first portion is arranged to face towards the individual.

3. The pressure sensing mat of claim 1, wherein the second direction is substantially orthogonal to the first direction.

4. The pressure sensing mat of claim 1, wherein conductive strips of the first plurality of conductive strips are formed as columns including first and second columns, wherein the first column has a first width and the second column has a second width greater than the first width.

5. The pressure sensing mat of claim 4, wherein the first column is spaced apart from a first end of the first portion by a first distance and the second column is spaced apart from the first end by a second distance.

6. The pressure sensing mat of claim 5, wherein intermediate columns are disposed between the first column and the second column, wherein intermediate widths of the intermediate columns differ from the first and second widths.

7. The pressure sensing mat of claim 2, wherein when the pressure sensing mat is used to detect pressure of the individual, the second end of the mat is configured to be arranged beneath a head of the individual.

8. The pressure sensing mat of claim 6, wherein the intermediate widths monotonically increase or decrease.

9. The pressure sensing mat of claim 4, wherein the second non-conductive layer includes a fourth plurality of discontinuities corresponding to the third plurality of discontinuities.

10. The pressure sensing mat of claim 9, wherein the second conductive layer is disposed between the second non-conductive layer and the insulative layer.

11. The pressure sensing mat of claim 1, wherein the first conductive layer is disposed between the first non-conductive layer and the insulative layer.

12. A pressure sensing mat comprising:
a first portion including a first conductive layer contacting a first non-conductive layer, wherein the first non-conductive layer and the first conductive layer define a first set of channels at least partially enclosing a first conductive strip extending in a first direction, wherein the first portion includes a first set of conductive leads and a second set of conductive leads, wherein the first set of conductive leads are disposed in a connecting region of the pressure sensing mat including a peripheral area and a medial area, wherein the first set of conductive leads includes a first conductive lead and a second conductive lead, wherein the first conductive lead has a first length and is disposed in the peripheral area and the second conductive lead has a second length, greater than the first length and is disposed in the medial area;
a second portion including a second conductive layer contacting a third non-conductive layer, wherein the third non-conductive layer and the second conductive layer define a second set of channels at least partially enclosing a second conductive strip extending in a second direction; and
an insulative layer disposed between the first portion and the second portion, wherein the first conductive strip and the second conductive strip form a capacitor configured to provide a capacitance indicative of a pressure applied to the capacitor.

13. The pressure sensing mat of claim 12, wherein the first set of channels at least partially enclose a third conductive strip and the second set of channels at least partially enclose a fourth conductive strip, wherein the third conductive strip and the fourth conductive strip form a second capacitor configured to provide a capacitance indicative of a pressure applied to the second capacitor.

14. The pressure sensing mat of claim 13, wherein the first conductive strip is disposed in a left region of the first portion and the third conductive strip is disposed in a right region of the first portion.

15. The pressure sensing mat of claim 14, wherein the first and third conductive strips are bounded by the first and second sets of conductive leads.

16. The pressure sensing mat of claim 12, wherein the first set of conductive leads are formed by a third set of channels extending substantially in the second direction and defined by the first non-conductive layer and the first conductive layer.

17. The pressure sensing mat of claim 12, wherein the first set of conductive leads are formed by a fourth set of channels extending in the first direction and defined by the first non-conductive layer and the first conductive layer.

18. The pressure sensing mat of claim 12, wherein the first set of conductive leads are disposed between a first side of the first conductive strip and a first side edge of the first conductive layer and the second set of conductive leads are disposed between a second side of the conductive strip and a second side edge of the first conductive layer, wherein the second side edge opposes the first side edge.

19. The pressure sensing mat of claim 12, wherein the first set of conductive leads include a number of conductive leads disposed between the first conductive lead and the second conductive lead, wherein a length of the each of the conductive leads disposed between the first conductive lead and the second conductive lead monotonically decreases from the peripheral area to the medial area.

20. The pressure sensing mat of claim 19, wherein the second set of conductive leads includes a first segment, a second segment, and a third segment, wherein the first segment is disposed on the second side of the first portion, the second segment extends in the first direction from the first set of signal detecting leads, and the third segment extends from the second segment.

21. The pressure sensing mat of claim 20, wherein the first segment is substantially orthogonal to the second segment.

22. The pressure sensing mat of claim 20, wherein at least one of the conductive leads of the first set of conductive leads has a first width and the first conductive strip has a second width greater than the first width.

23. The pressure sensing mat of claim 12, wherein the first conductive layer has a first surface area, the first non-conductive layer has a second surface area, wherein the first surface area is greater than the second surface area.

24. The pressure sensing mat of claim 12, wherein the first portion has a first thickness wherein the first set of channels has a first depth that is less than the first thickness.

25. The pressure sensing mat of claim 12, wherein the first non-conductive layer is laminated to the conductive layer.

26. The pressure sensing mat of claim 12, wherein the first conductive layer is formed of copper.

27. The pressure sensing mat of claim 26, wherein the first conductive layer has a surface resistivity of at least 0.10 ohms.

* * * * *